(12) United States Patent
Ethington et al.

(10) Patent No.: US 12,384,383 B1
(45) Date of Patent: Aug. 12, 2025

(54) SYSTEMS AND METHODS FOR CONTROLLING VEHICLE SYSTEMS BASED ON DRIVER ASSESSMENT

(71) Applicant: United Services Automobile Association (USAA), San Antonio, TX (US)

(72) Inventors: Seth E. Ethington, McKinney, TX (US); William Daniel Farmer, Carrollton, TX (US); Pooja Krishnaswamy, Cedar Park, TX (US); Timothy Shiveley, Farmers Branch, TX (US); Anto Chirayil Thomas, Coppell, TX (US); Daniel Scott Veibell, Plano, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 0 days.

(21) Appl. No.: 18/419,256

(22) Filed: Jan. 22, 2024

Related U.S. Application Data

(63) Continuation of application No. 17/892,867, filed on Aug. 22, 2022, now Pat. No. 11,878,699, which is a
(Continued)

(51) Int. Cl.
*B60W 40/09* (2012.01)
*A61B 5/00* (2006.01)
(Continued)

(52) U.S. Cl.
CPC ............. *B60W 40/09* (2013.01); *A61B 5/162* (2013.01); *A61B 5/18* (2013.01); *A61B 5/6802* (2013.01);
(Continued)

(58) Field of Classification Search
CPC ................ B60W 40/09; B60W 40/02; B60W 2040/0872; B60W 2540/221;
(Continued)

(56) References Cited

U.S. PATENT DOCUMENTS 8,560,010 B2 10/2013 Koehn
9,135,803 B1 9/2015 Fields et al.
(Continued)

*Primary Examiner* — Ryan W Sherwin
(74) *Attorney, Agent, or Firm* — Fletcher Yoder, P.C.

(57) ABSTRACT

A system may include sensors that may acquire health data related to an individual. The system may also include a processor that may receive trip data associated with a current location of the individual and a destination location for the individual, traffic condition data associated with routes between the current location and the destination location, and weather related data associated with the routes. The processor may also receive the health data from the sensors and determine whether the individual is associated with a driver assessment score above a threshold based on the trip data, the traffic condition data, the weather data, the health data, or any combination thereof. The processor may then send an activation signal to a vehicle control system in response to the driver assessment score being above the threshold, such that the activation signal may enable the vehicle control system to control operations of a vehicle.

20 Claims, 2 Drawing Sheets

Related U.S. Application Data continuation of application No. 17/004,942, filed on Aug. 27, 2020, now Pat. No. 11,427,207.

(60) Provisional application No. 62/893,570, filed on Aug. 29, 2019.

(51) Int. Cl.
    *A61B 5/16*    (2006.01)
    *A61B 5/18*    (2006.01)
    *B60W 40/02*    (2006.01)
    *G06Q 50/40*    (2024.01)
    *B60W 40/08*    (2012.01)

(52) U.S. Cl.
CPC ............ *B60W 40/02* (2013.01); *G06Q 50/40* (2024.01); *B60W 2040/0872* (2013.01); *B60W 2540/221* (2020.02); *B60W 2540/229* (2020.02); *B60W 2540/30* (2013.01)

(58) Field of Classification Search
CPC ........ B60W 2540/229; B60W 2540/30; A61B 5/162; A61B 5/18; A61B 5/6802; G06Q 50/40

See application file for complete search history.

(56) References Cited

U.S. PATENT DOCUMENTS

| | | |
|---|---|---|
| 9,141,582 B1 | 9/2015 | Brinkmann et al. |
| 9,501,928 B1 | 11/2016 | Bell et al. |
| 10,163,274 B1 | 12/2018 | Brinkmann et al. |
| 10,278,634 B2 | 5/2019 | Cogill et al. |
| 10,618,523 B1 | 4/2020 | Fields et al. |
| 10,703,379 B1 | 7/2020 | Harvey et al. |
| 11,427,207 B1 | 8/2022 | Ethington et al. |
| 12,013,695 B1* | 6/2024 | Fields ................. G05D 1/0088 |
| 2003/0146841 A1 | 8/2003 | Koenig |
| 2006/0227047 A1* | 10/2006 | Rosenberg ............ G01S 5/0054 342/357.55 |
| 2007/0120691 A1 | 5/2007 | Braun |
| 2007/0222617 A1 | 9/2007 | Chai et al. |
| 2008/0114638 A1* | 5/2008 | Colliau ............... G06Q 10/1095 705/7.19 |
| 2008/0234927 A1* | 9/2008 | O'Neill .................. G01C 21/34 701/465 |
| 2009/0043486 A1* | 2/2009 | Yang .................. G01C 21/3492 701/117 |
| 2009/0118995 A1* | 5/2009 | Zhao ................. G08G 1/096844 701/414 |
| 2014/0275834 A1 | 9/2014 | Bennett |
| 2014/0276090 A1 | 9/2014 | Breed |
| 2015/0039175 A1 | 2/2015 | Martin et al. |
| 2015/0038123 A1 | 12/2015 | Tuukkanen et al. |
| 2015/0375756 A1 | 12/2015 | Do et al. |
| 2016/0046298 A1* | 2/2016 | DeRuyck ............. B60K 28/066 340/576 |
| 2016/0311423 A1 | 10/2016 | Storm |
| 2016/0364678 A1* | 12/2016 | Cao ....................... G06Q 10/083 |
| 2017/0076395 A1* | 3/2017 | Sedlik .................... G08G 1/012 |
| 2017/0088142 A1 | 3/2017 | Hunt et al. |
| 2017/0191847 A1* | 7/2017 | Chintakindi ....... G01C 21/3484 |
| 2017/0213273 A1* | 7/2017 | Dietrich ............. G06Q 20/4016 |
| 2017/0242433 A1 | 8/2017 | Ochiai et al. |
| 2018/0075380 A1 | 3/2018 | Perl et al. |
| 2018/0164108 A1 | 6/2018 | Rahal-Arabi et al. |
| 2018/0173866 A1* | 6/2018 | Williams ............... G16H 40/67 |
| 2018/0196427 A1 | 7/2018 | Majumdar et al. |
| 2018/0211337 A1* | 7/2018 | Ghaddar ................ G06Q 50/14 |
| 2019/0016343 A1* | 1/2019 | Allen ..................... G06Q 50/40 |
| 2019/0102840 A1* | 4/2019 | Perl .......................... G06N 3/08 |
| 2019/0171988 A1* | 6/2019 | Kwatra ................. G06Q 50/40 |
| 2019/0225232 A1 | 7/2019 | Blau |
| 2020/0070848 A1 | 3/2020 | Ozer |
| 2020/0130688 A1 | 4/2020 | Kline et al. |
| 2020/0231179 A1* | 7/2020 | Tian .................. G01C 21/3697 |
| 2021/0016805 A1 | 1/2021 | Oba et al. |

\* cited by examiner

SYSTEMS AND METHODS FOR CONTROLLING VEHICLE SYSTEMS BASED ON DRIVER ASSESSMENT

CROSS-REFERENCE TO RELATED APPLICATION

This application is a continuation of U.S. patent application Ser. No. 17/892,867, titled "Systems and Methods for Controlling Vehicle Systems Based on Driver Assessment," filed on Aug. 22, 2022, which is a continuation of U.S. patent application Ser. No. 17/004,942, titled "Systems and Methods for Controlling Vehicle Systems Based on Driver Assessment," filed on Aug. 27, 2020, which claims priority to and benefit of U.S. Provisional Patent Application Ser. No. 62/893,570, titled "Systems and Methods for Controlling Vehicle Systems Based on Driver Assessment," filed on Aug. 29, 2019, the entirety of which is incorporated by reference into the present disclosure.

BACKGROUND

The present disclosure relates generally to controlling a vehicle system used to operate a vehicle based on an assessment performed on a potential driver. More specifically, the present disclosure relates to assessing various properties associated with the driver and controlling access to drive the vehicle based on the various properties.

As vehicle driving systems become more capable of receiving and analyzing data from various data sources, the vehicle driving systems may use the acquired and analyzed data to control certain vehicle operations. Indeed, the increased vehicle operation controls may ensure that the vehicles that are operating on roadways are operating in such a manner that reduces the likelihood of accidents.

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a system may include one or more sensors that may acquire health data related to an individual. The system may also include a processor that may receive trip data associated with a current location of the individual and a destination location for the individual, traffic condition data associated with one or more routes between the current location and the destination location, and weather related data associated with the one or more routes. The processor may also receive the health data from the one or more sensors and determine whether the individual is associated with a driver assessment score above a threshold based on the trip data, the traffic condition data, the weather data, the health data, or any combination thereof. The processor may then send an activation signal to a vehicle control system in response to the driver assessment score being above the threshold, such that the activation signal may enable the vehicle control system to control one or more operations of a vehicle.

In yet another embodiment, a method may include receiving, via a processor, trip data associated with a current location of the individual and a destination location for the individual, receiving traffic condition data associated with one or more routes between the current location and the destination location, and receiving weather data associated with the one or more routes, and receiving health data from one or more sensors disposed in a computing device. The method may then involve determining a driver assessment score based on the trip data, the traffic condition data, the weather data, the health data, or any combination thereof and sending a request to a ride share system in response to the driver assessment score being below a threshold.

In another embodiment, a non-transitory computer-readable medium may include computer-executable instructions that, when executed by a processor, are configured to cause the processor to perform operations that may include receiving trip data associated with a current location of the individual and a destination location for the individual. The operations may also include receiving traffic condition data associated with one or more routes between the current location and the destination location, receiving weather data associated with the one or more routes, and receiving health data from one or more sensors disposed in a computing device. After receiving the data, the operations may include determining a driver assessment score based on the trip data, the traffic condition data, the weather data, and the health data. The operations may then involve sending a command to a vehicle control system to allow access to one or more operations of a vehicle in response to the driver assessment score being above a threshold.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
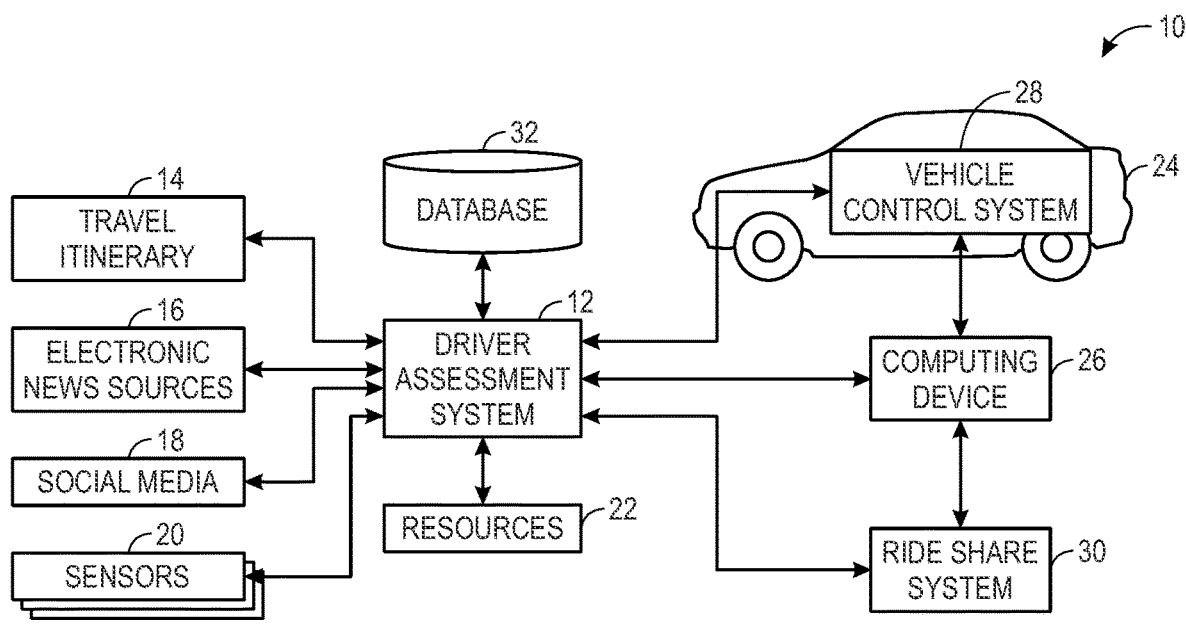
FIG. 1 illustrates a block diagram of a system for assessing driver properties and controlling vehicles, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. It should be noted that the term "multimedia" and "media" may be used interchangeably herein.

Information regarding various aspects of an environment is readily available for use by a wide variety of software applications. For example, information regarding weather conditions present in a particular area may be accessible by a computing device via the Internet or some other electronic new source. Using weather information as an example, in certain embodiments, a monitoring system may track a location of an individual and determine whether the individual is at risk of encountering undesirable weather conditions based on his location and corresponding weather conditions. If the monitoring system determines that the risk of encountering the undesirable weather conditions is greater than some threshold, the monitoring system may send a recommended action to the individual to undertake in order to avoid or mitigate a risk of property or personal damage in light of the undesirable weather.

With this in mind, driving conditions may change at various times due to various properties, such as weather, traffic conditions, and the like. In the same manner, an individual may have physical properties that change at various times, such that the physical properties may relate to the individual's ability or proficiency in driving. By analyzing the driving conditions in light of an individual's physical conditions, a driver assessment system may determine whether the individual is associated with a higher risk for experiencing an incident (e.g., accident) while driving with the detected driving conditions and physical properties. Based on this determination, the driver assessment system may send control signal to a vehicle control system that controls the operation of a vehicle. That is, if the driver assessment system determines that the driving conditions are suitable for the individual having the detected physical properties to driver, the driver assessment system may allow the driver to control and operate the vehicle. Additional details with regard to the driver assessment system and embodiments in which the driver assessment system may control the operation of the vehicle control system will be discussed below.

By way of introduction, FIG. 1 illustrates a block diagram of a system 10 in which a driver assessment system 12 may receive data that may be used to assess the ability of an individual to drive a vehicle in certain driving conditions. Referring to FIG. 1, the driver assessment system 12 may receive data from various sources. The received data may be related to current driving conditions and current physical conditions of the driver. Using the collected data, the driver assessment system 12 may determine a risk of a driver injuring himself or some property. That is, the driver assessment system 12 may analyze the collected data to assess the driver's ability to drive under the current driving conditions and in light of the current physical properties of the driver to determine a risk or potential for damage to occur to another individual or property. If the risk exceeds a threshold, the driver assessment system 12 may send a control signal to a vehicle control system to prevent the vehicle from being operated. Alternatively, the driver assessment system 12 may modify other operating parameters (e.g., radio, air conditioning, cruise control) of the vehicle based on the determined risk.

In some embodiments, the driver assessment system 12 may be any suitable computing or server device. Using data sources (e.g., databases, weather services, new services, sensors) accessible to the driver assessment system 12, the driver assessment system 12 may receive data regarding driving conditions within a geographical region associated with the location of the driver assessment system 12. Additionally, the driver assessment system 12 may receive data including environmental information associated with the location of the driver assessment system 12. For example, the driver assessment system 12 may receive data from sources such as travel itinerary 14, electronic news sources 16, social media 18, sensors 20, and other resources 22.

The travel itinerary 14 may include information regarding locations in which an individual associated with the driver assessment system 12 may be traveling. The travel itinerary 14 may be acquired by mining data sources such as emails, text messages, electronic calendar items, and the like. In some embodiments, the travel itinerary 14 may be directly input into the driver assessment system 12 as a component of a mapping program that provides a recommended route (e.g., a route for a car) to a destination. In some embodiments, the driver assessment system 12 may adjust the generated route based on the analysis described below. In certain embodiments, the driver assessment system 12 may be associated with a travel services organization that may assist the individual in scheduling the itinerary for an upcoming trip. The travel services organization may thus provide the data regarding the travel itinerary 14.

The electronic news sources 16 may include various news services that may be updated in real time or near real time via a network (e.g., Internet). The electronic news sources 16 may provide information regarding weather alerts, natural disaster alerts, non-natural disaster alerts (e.g., traffic, active shooter), and any other information that may be published via an electronic news outlet such as a webpage, news database, or the like.

The social media 18 may include data available via social media sites such as Facebook®, Twitter®, and the like. In one embodiment, the social media 18 may be associated with the individual employing the driver assessment system 12. For example, social media 18 associated with the location of a user or a destination of the user may be considered. The social media 18 may also include data trending on social media sites that may not be directly associated with the individual. The data from the social media 18 may include information regarding a natural disaster, dangerous situation (e.g., active shooter), and the like. In some embodiments, the social media 18 may include crowd source data that is updated in real time (e.g., near instantaneous). Although the crowd source data may not be verified by news sources, it can often provide information related to a disruptive event (e.g., active shooter, accident) more quickly than certain electronic news sources.

The sensors 20 may include any type of device capable of measuring location, pressure, moisture, temperature, light, and the like. One or more sensors 20 may be disposed on different types of property, such as a home, a vehicle, and the like. In certain embodiments, one or more sensors 20 may be disposed within certain rooms of the home, outside the home, within the vehicle, or outside the vehicle. The sensors 20 may also be disposed on devices carried by or worn by individuals. For example, the sensors may be disposed on mobile phones, wearable electronics, and the like. In one embodiment, the sensors 20 may provide location information regarding the sensors 20. As such, the sensors 20 may provide global positioning system (GPS) coordinates and the like to indicate a location of the sensors 20.

In addition, the sensors 20 may provide data regarding the physical properties associated with an individual wearing the sensor 20. For example, the sensors 20 disposed on wearable devices may detect health-related data, such as a heartrate, electrocardiogram data, moisture (e.g., sweat), and the like. In some embodiments, if the individual's health-related data exceeds or is less than some threshold, the driver assessment system 12 may increase or decrease a calculated risk associated with the individual driving a vehicle. For instance, if the detected heart rate of an individual is outside of a range of acceptable values, the driver assessment system 12 may increase a risk value associated with the driver operating a vehicle 24.

The sensors 20 may also measure activity properties associated with the individual, such as a number of steps, an amount of exercise performed, an amount of flights climbed, and the like. In some embodiments, if the individual performed a certain amount of activity that exceeded some threshold, the driver assessment system 12 may increase a calculated risk associated with the individual driving a vehicle.

The sensors 20 may also include an image sensor that may acquire image data of the individual. The image data concerning an individual may provide information related to the current state of health of the individual. For example, recently acquired image data may be compared to previously acquired image data to assess a health of an individual.

Keeping this in mind, in one embodiment, an image of an eye of an individual may provide an indication regarding the individual's current visibility capabilities. That is, some individuals may experience vision capabilities that vary at various times (e.g., day, week, month). In other words, the individual's vision may be better suited to detect objects in low light (e.g., dawn, dusk) environments on certain days, as opposed to having the same ability every day. As such, in some embodiments, the driver assessment system 12 may acquire the image data of an eye of an individual after receiving a request from the individual to operate the vehicle 24. In response to receiving the request, the driver assessment system 12 may perform a driving assessment test that may assist the driver assessment system 12 to ascertain the current driving ability of the individual. The test may be designed to test the amount of time that the individual's eye responds to certain stimuli. For example, if the driver assessment system 12 is implemented via a smart phone or other suitable computing device, the driver assessment system 12 may display image data on a display of the smart phone while tracking the eye movement of the individual via an image sensor disposed on the same side of the display. The display may present images that may cause the individual's eye to move, and the driver assessment system 12 may measure the response time for the individual's eye to move in an expected fashion.

In another embodiment, the sensors 20 may measure an amount of pressure or tension, which may provide the driver assessment system 12 with an indication of the individual's current health state. For example, the sensors 20 may be disposed on a smart phone or other suitable device, and the individual may squeeze or pull certain attributes of the smart phone, such that the sensors 20 may measure the individual's grip strength or the force exerted by the individual on the sensors 20. The grip strength or detected force may be associated with cardiac properties of the individual. That is, if the grip strength corresponds to an expected grip strength of the individual, as determined during a baseline assessment of the individual, the driver assessment system 12 may determine that the cardiac properties (e.g., heart rate, heart stability, blood pressure) is suitable for driving. In some embodiments, if the individual's grip strength was less than some threshold, the driver assessment system 12 may increase a calculated risk associated with the individual driving a vehicle.

The sensors 20 may also include medical devices that invasively measure certain properties related to a body chemistry or other physical traits internal to the individual. The physical traits may include a blood sugar level, blood alcohol level, a cholesterol level, an electrolyte level, or other measurable traits. As such, by way of example, the sensors 20 may include patch pumps, bolus injectors, biosensors, and other body-worn diagnostic devices.

Referring back to FIG. 1, the resources 22 may include any other electronic information that may be available via a network, the Internet, or the like. In certain embodiments, the resources 22 may include additional information regarding the individual or a group of individuals having similar demographics of the individual. For example, the resources 22 may include data, such as a residential address of an individual, a business address of the individual, information related to whether the individual works at home, whether the individual is associated with a particular organization (e.g., school) or group, and other information that may provide insight regarding a location of the individual at various times during the week.

With the foregoing in mind, the driver assessment system 12 may receive data from the various sources described above and determine a risk associated with the individual driving the vehicle 24. After determining that the risk is above some threshold, the driver assessment system 12 may send a notification or alert to a computing device 26 associated with the individual via a network or via a direct communication link. The driver assessment system 12 and the computing device 26 may include any suitable computing device such as a general-purpose computer, a mobile computing device, a laptop-computing device, a tablet computing device, a wearable computing device, and the like. Additional details with regard to the driver assessment system 12 will be discussed below with reference to FIG. 2.

After receiving the notification, the computing device 26 may display the notification via a text message, an email message, an alert, or the like. In any case, the notification may provide a warning with regard to the likelihood of risk of injury or damage, an environmental condition associated with the risk, recommendations to reduce the risk of injury or damage, or the like. In addition, the driver assessment system 12 may automatically send a command to a vehicle control system 28 of the vehicle 24 based on the risk or other parameters evaluated by the driver assessment system 12. The command may cause the vehicle control system 28 to allow the vehicle 24 to be engaged or driven by the individual, prevent the vehicle 24 from being operated, limit operating parameters (e.g., radio, speed, operating radius, freeway driving) of the vehicle 24, and the like.

In some embodiments, the driver assessment system 12 may send a request to a ride share system 30 based on the risk or other parameters evaluated by the driver assessment system 12. The ride share system 30 may be communicatively coupled to a number of drivers that facilitate a taxi or driving service to assist the individual in reaching a particular location. As such, the ride share system 30 may receive requests from various individuals that include a current location of the individuals and a requested destination for the individuals. The ride share system 30 may identify drivers that are nearby the current location of the individual and allow one of the drivers to accept the proposal to drive the individual to the requested destination. In any case, since the driver assessment system 12 is controlling the operation of the vehicle 24 while coordinating access to the ride share system 30, the driver assessment system 12 may be equipped to better control the individual's risk associated with driving the vehicle 24. Additional details with regard to the driver assessment system 12 controlling the operation of the vehicle 24 or coordinating a request for a ride via the ride share system 30 will be discussed with respect to FIG. 3 below.

After sending the notification to the computing device 26, the driver assessment system 12 may store data related to the notifications transmitted to the computing device 26, the requests to the ride share system 30, the commands transmitted to the vehicle control system 28, and other detected data in a database 32. The driver assessment system 12 may also store information regarding any determinations made by or data acquired by the driver assessment system 12. For example, the driver assessment system 12 may store the data acquired via the sensors 20 or the environmental information gleaned from the electronic news sources 16, the social media 18, the resources 22, or the like. Additionally, driver assessment system 12 may store information regarding the behavior of the individual based on the data gathered via sensors 20, the travel itinerary 14, the resources 22, and the like.

Figure 2:
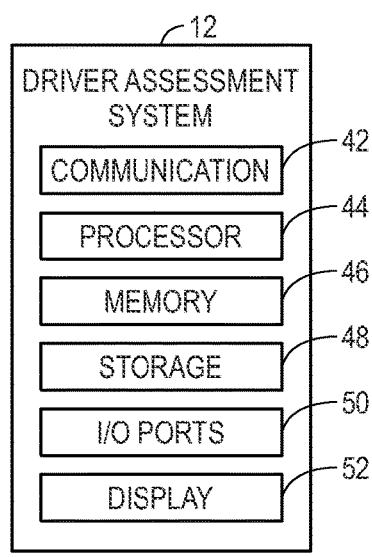
FIG. 2 illustrates a block diagram of a driver assessment system that may be part of the system of FIG. 1, in accordance with embodiments described herein.

To perform some of the actions set forth above, the driver assessment system 12 may include certain components to facilitate these actions. FIG. 2 is a block diagram of example components within driver assessment system 12. For example, driver assessment system 12 may include a communication component 42, a processor 44, a memory 46, a storage 48, input/output (I/O) ports 50, a display 52, and the like. The communication component 42 may be a wireless or wired communication component that may facilitate communication between driver assessment system 12, the sensors 20, the vehicle control system 28, the ride share system 30, the database 32, the computing device 26, and the like. Additionally, the communication component 42 may facilitate data transfer to driver assessment system 12, such that driver assessment system 12 may receive the travel itinerary 14, the electronic news sources 16, the social media 18, the resources 22, and the like.

The processor 44 may be any type of computer processor or microprocessor capable of executing computer-executable code. The processor 44 may also include multiple processors that may perform the operations described below.

The memory 46 and the storage 48 may be any suitable articles of manufacture that can serve as media to store processor-executable code, data, or the like. These articles of manufacture may represent computer-readable media (e.g., any suitable form of memory or storage) that may store the processor-executable code used by the processor 44 to perform the presently disclosed techniques. The memory 46 and the storage 48 may also be used to store data described, various other software applications for analyzing the data, and the like. The memory 46 and the storage 48 may represent non-transitory computer-readable media (e.g., any suitable form of memory or storage) that may store the processor-executable code used by the processor 44 to perform various techniques described herein. It should be noted that non-transitory merely indicates that the media is tangible and not a signal.

The I/O ports 50 may be interfaces that may couple to other peripheral components such as input devices (e.g., keyboard, mouse), sensors, input/output (I/O) modules, and the like. The display 52 may operate to depict visualizations associated with software or executable code being processed by the processor 54. In one embodiment, the display 52 may be a touch display capable of receiving inputs from a user of driver assessment system 12. The display 52 may be any suitable type of display, such as a liquid crystal display (LCD), plasma display, or an organic light emitting diode (OLED) display, for example. Additionally, in one embodiment, the display 52 may be provided in conjunction with a touch-sensitive mechanism (e.g., a touch screen) that may function as part of a control interface for driver assessment system 12.

It should be noted that the components described above with regard to driver assessment system 12 are exemplary components and driver assessment system 12 may include additional or fewer components as shown. Additionally, it should be noted that the computing device 26, the vehicle control system 28, and the ride share system 30 may also include similar components as described as part of driver assessment system 12.

Figure 3:
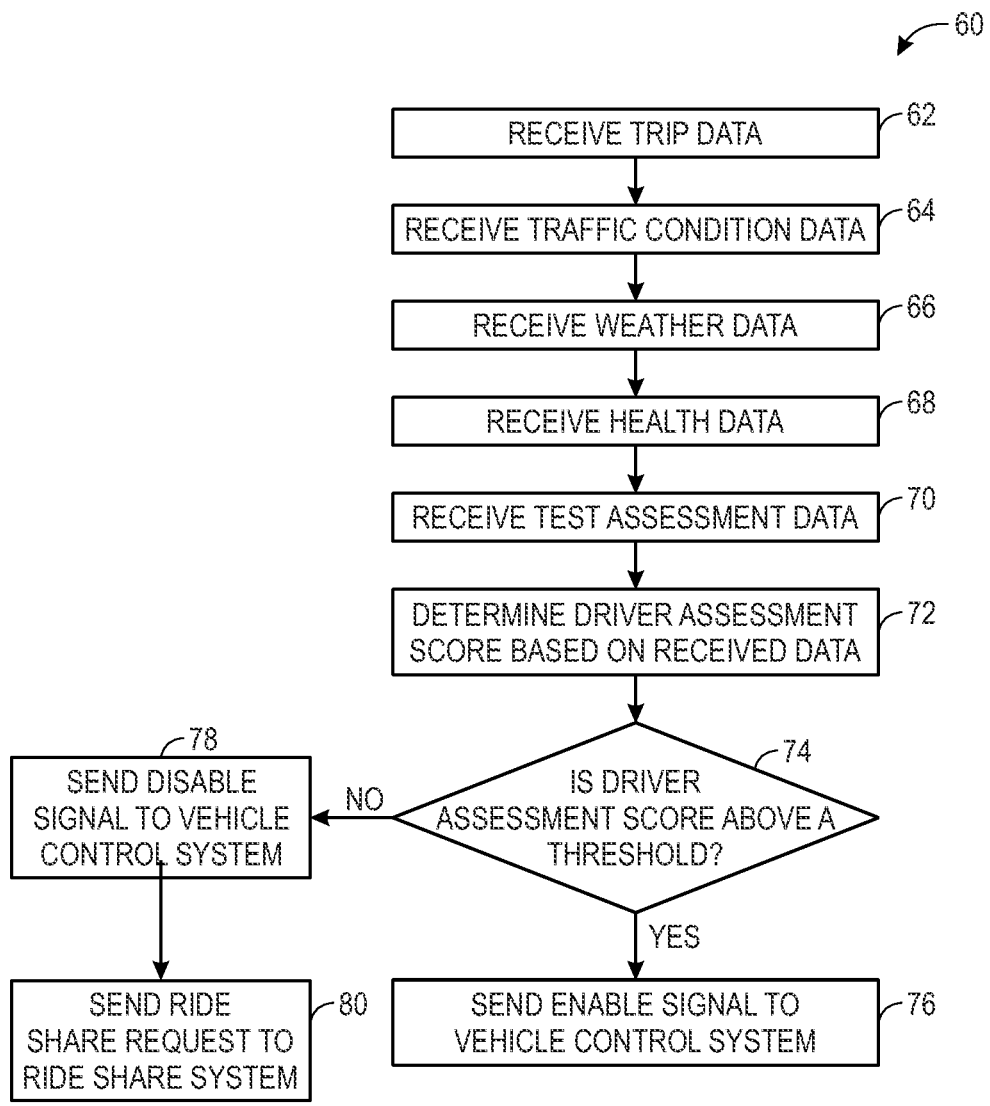
FIG. 3 illustrates a flow chart of a method for controlling a vehicle system based on data acquired by the driver assessment system, in accordance with embodiments described herein.

With the foregoing in mind, FIG. 3 illustrates a flow chart of a method 60 employed by the driver assessment system 12 for sending control signals to the vehicle control system 28, sending requests to the ride share system 30, or both based on an assessment of an individual's driving abilities. Although the following description of the method 60 is described in a particular order, it should be noted that the method 60 is not limited to the depicted order; and, instead, the method 60 may be performed in any suitable order. In addition, although the driver assessment system 12 is described as performing the method 60, it should be understood that the method 60 may be performed by any suitable computing device including, for instance, the computing device 26 and the like.

Referring now to FIG. 3, at block 62, the driver assessment system 12 may receive trip data related to an individual's desire to travel to a location via the vehicle 24. As discussed above, the driver assessment system 12 may receive data from various sources, the data including the travel itinerary 14, the electronic news sources 16, the social media 18, the sensors 20, the resources 22, and the like. Generally, the trip data received at block 62 may provide information regarding the current location of the individual and a destination location for the individual. In some embodiments, the trip data may be a request to the driver assessment system 12 that indicates that the individual requests access to drive the vehicle 24. In another example, the driver assessment system 12 may mine the driver's emails, web browsing records, social media data 18, or other suitable information source to predict a location that the driver intends to visit.

At block 64, the driver assessment system 12 may receive traffic condition data related to the current or expected traffic conditions associated with a driving trip from the individual's current location to the individual's destination location at the expected time in which the driver is requesting to use the vehicle 24. The traffic conditions may be retrieved from the electronic news sources 16, the social media 18, the sensors 20, the resources 22, the database 32 (e.g., empirical traffic data for previous trips to the destination location), and the like. The traffic conditions may include data related to whether an accident is present along one or more routes that may be used for the trip, whether construction is present along the routes, whether road closures are present along the routes, an amount of vehicles present along the routes, an indication with regard to a relative amount of vehicle congestion along the routes as compared to other times, an average speed in which traffic flows along the routes, and the like. The traffic conditions may also include data related to social conditions (e.g., traffic, social unrest, active shooter) within the vicinity or approaching the location of the individual, along the routes of the trip for the individual, and the like.

Additionally, at block 66, the driver assessment system 12 may receive weather or environment data regarding environment conditions (e.g., weather) along the routes of the individual's trip. The weather data may include data related to whether precipitation (e.g., rain, hail, snow) is expected along the routes of the desired trip. In addition, the weather data may include an indication of certain weather advisories such as a thunderstorm, flash flood, tornado, or other weather-related events that may affect the individual's ability to drive the vehicle 24.

At block 68, the driver assessment system 12 may receive health-related data associated with the individual's current health condition or driving abilities. As mentioned above, the health-related data may include data related to an amount of activity (e.g., steps, flights climbed, calories burned) performed by the individual over a period of time. In addition, certain sensors 20, which may be disposed on the driver assessment system 12, may detect certain physical properties associated with the individual via the sensors 20, as described above with reference to FIG. 1. The health-related data may include any type of data that may be relevant to the individual's current health status or ability to drive. For example, if the individual is diagnosed with diabetes and the health-related data indicates that his blood-sugar level is less than some threshold, the individual's ability to drive may be affected by the lack of sugar in the blood.

In another example, if the individual's health activity (e.g., number of steps, calories burned) is less than some threshold, the driver assessment system 12 may be configured to prevent or limit the driving of the driver. In this way, the driver assessment system 12 may be programmed or configured by guardians to provide health incentives for drivers to pursue in order to have the ability to drive the vehicle 24.

At block 70, the driver assessment system 12 may receive test assessment data, which may correspond to the individual's current health status or driving ability. As discussed above in FIG. 1, the driver assessment system 12 may present certain tasks via the display 52 to assess certain aspects of the individual's current health status. The tests may assess the individual's reflex ability or may measure the amount of time that the individual uses to respond to certain stimuli, such as visual stimuli presented via the display 52. As discussed above, an image sensor of the driver assessment system 12 may track or measure the individual's eye movement, such that the driver assessment system 12 may measure the response time of the individual.

In another embodiment, the driver assessment system 12 may output audio data via a speaker or other suitable device, such that the audio data includes a request that the individual answer certain questions. The individual's responses to the questions may be received via audio sensors (e.g., microphone), and the driver assessment system 12 may analyze the answers to detect voice inflections or may compare the received audio to stored audio responses from the individual to detect whether the individual is lying or in a non-normal state. That is, an individual's voice may have certain voice inflections or patterns that may be measured via the respective sound waves produced by the individual. The produced sound waves may be compared to stored audio data having sound waves representative of the individual's voice when in a healthy state.

After receiving the various types of data in blocks 62-70, the driver assessment system 12 may, at block 72, determine a driver assessment score using one or more of the received datasets. The driver assessment system 12 may analyze the received data in a number of ways. For example, the driver assessment system 12 may assign a weight to each type of data based on known health-related issues, may evaluate each data type individually, or the like. In any case, a number of example analysis methods will be described below; however, it should be noted that the manner in which the driver assessment system 12 may assess the individual's driving ability should not be limited to those described below.

In one example, the driver assessment system 12 may determine a dataset to use to determine the driver assessment score based on the current location of the individual or the destination location of the individual. That is, if either location is associated with a place in which the individual's driving abilities may be reduced, the driver assessment system 12 may prioritize or assign a relatively higher weight to the trip data. By way of example, if the current location of the individual is associated with a business that serves alcohol, the driver assessment system 12 may assign a higher weight value to the trip data and any other data received at blocks 64-70 that may be indicative of the individual's blood alcohol content. For example, the health-related data acquired via the sensors 20 may provide information related to the blood alcohol level of the individual. In the same manner, the test assessment data may measure the reflexes of the individual to ensure that the individual is not affected by alcohol.

In another example, if the trip data is indicative of an amount of time in the vehicle 24 exceeding a threshold amount of time, the driver assessment system 12 may increase the weights associated with the traffic condition data and the weather data. In addition, the driver assessment system 12 may determine whether any other collected data may be relevant to the individual's ability to drive for more than the threshold amount of time. For example, if the health-related data indicates that the individual has burned a threshold amount of calories and has been active or awake for a certain amount of time, the driver assessment system 12 may increase the weight applied to the relevant health data to assess the individual's ability to drive for the threshold amount of time.

In yet another embodiment, if the traffic condition data or the weather data is indicative of relatively congested traffic as compared to other hours during the day or inclement weather conditions expected to form, the driver assessment system 12 may increase the weight applied to the test assessment data to ensure that the individual is capable of driving under potentially stressful or challenging circumstances.

In any case, it should be understood that the driver assessment system 12 may adjust the weight applied to any dataset based on a combination of the circumstances that may be present. In this way, the driver assessment system 12 may more accurately assess the individual's driving ability in light of the variable conditions that may be present each time the individual drives.

With the foregoing in mind, the driver assessment score may be determined by summing together a raw score associated with each received dataset. That is, the trip data may be assessed a raw score between 0 and 100 based on the length of the drive. In the same manner, the traffic data may be assigned a raw score between 0 and 100 based on the amount of traffic or the amount of delay that the traffic conditions may cause. The weather data may also be assigned a raw score between 0 and 100 based on the conditions being hazardous for driving and clear for driving.

The health-related data and the test assessment data may also be assigned a raw score between 0 and 100 based on reference data points associated with the individual. As mentioned above, the driver assessment system 12 may compare the current health-related data or test assessment data with previously collected data from the individual to determine the individual's current health status. The amount of difference between the currently acquired data and the previously acquired data may be quantified into the respective raw score.

At block 74, the driver assessment system 12 may determine whether the driver assessment score exceeds some threshold. The threshold may be associated with an expected score for the individual. In other embodiments, the driver assessment system 12 may individually compare each received dataset with a respective threshold and determine a driver assessment score based on each dataset meeting the respective threshold expectations.

In another embodiment, the driver assessment system 12 may assess a portion or subset of the datasets received at blocks 62-70 to assess the individual's ability to drive. That is, the driver assessment system 12 may be programmed to evaluate certain datasets, which may be pre-selected by the individual or by the individual's insurance company, to determine the individual's current driving capabilities. As such, although the driver assessment system 12 is described as determining a driver assessment score, it should be noted that the score may be an evaluation or determination as to whether certain conditions or received datasets are present.

After evaluating the received datasets, if the driver assessment system 12 determines that the individual meets the threshold for driving the vehicle 24, the driver assessment system 12 may send an activation or authentication signal to the vehicle control system 28. In some embodiments, the driver assessment system 12 may provide a notification for view by the individual via the display 52, such that the individual is aware of receiving the activation or authentication signal. The activation or authentication signal may cause the vehicle control system 28 to allow the individual to drive the vehicle. In some embodiments, the vehicle control system 28 may receive biometric data or other identification data from the individual prior to allowing the vehicle to be operated. In this way, the vehicle control system 28 may allow the individual who is associated with the authentication signal to drive the vehicle.

Referring back to block 74, if the driver assessment system 12 determines that the driver assessment score or condition is less than the threshold, the driver assessment system 12 may proceed to block 78 and send a disable signal to the vehicle control system 28. The disable signal may cause the vehicle control system 28 to ignore requests to start or operate the vehicle 24.

At block 80, the driver assessment system 12 may then send a request to the ride share system 30 to facilitate a drive to the destination location for the individual. In some embodiments, the driver assessment system 12 may provide a notification for view via the display 52 or the like indicative of the disable signal being sent to the vehicle control system 28, the request for the ride share being transmitted, and the like to inform the individual that his request to operate the vehicle was denied.

By performing the embodiments described herein, the driver assessment system 12 may control the risk associated with an individual driving a vehicle in certain environmental conditions and in light of certain individual health-related conditions. These techniques may be used to control the operations of a vehicle and efficiently provide an individual with access to a ride share system to reduce the risks associated with driving.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A method, comprising:
receiving, via at least one processor, trip data associated with a current location, a destination location, and an expected amount of time that an individual will be in a vehicle for each of one or more routes between the current location and the destination location;
receiving, via the at least one processor, weather data associated with the one or more routes between the current location and the destination location;
receiving, via the at least one processor, test assessment data indicative of health characteristics of the individual, wherein the test assessment data is determined based on a driving assessment test performed in response to a request from the individual to operate the vehicle;
determining a first weight based on the expected amount of time that the individual will be in the vehicle;
determining a second weight based on the weather data;
assigning, via the at least one processor, the first weight to the weather data and the second weight to the test assessment data to generate weighted weather data and weighted test assessment data;
determining, via the at least one processor, a driver assessment score based on the weighted weather data and the weighted test assessment data, wherein the driver assessment score is associated with a risk of injury associated with the individual driving a vehicle to the destination location in view of the weighted weather data and the weighted test assessment data;
determining, via the at least one processor, whether the driver assessment score is above a threshold; and
sending, via the at least one processor, a signal to a vehicle control system in response to the driver assessment score being above the threshold, wherein the signal is configured to cause the vehicle control system to allow access to control one or more operations of the vehicle.

2. The method of claim 1, comprising sending a request for a ride to a ride share system in response to the driver assessment score being below the threshold.

3. The method of claim 1, wherein the test assessment data corresponds to an amount of time that an eye takes to respond to a stimulus.

4. The method of claim 1, wherein the test assessment data corresponds to an assessment of a current ability of the individual to drive.

5. The method of claim 1, wherein the test assessment data is received from one or more sensors disposed in a device.

6. The method of claim 5, wherein the device comprises a mobile phone.

7. The method of claim 1, wherein the test assessment data corresponds to a pressure value associated with the individual.

8. A method, comprising:
  receiving, via a processor, trip data associated with a current location, a destination location, and an expected amount of time that an individual will be in a vehicle for each of one or more routes between the current location and the destination location;
  receiving, via the processor, traffic condition data associated with one or more routes between the current location and the destination location;
  receiving, via the processor, test assessment data from one or more sensors disposed in a computing device, wherein the test assessment data is determined based on a driving assessment test performed in response to a request from the individual to operate the vehicle;
  determining a first weight based on the expected amount of time that that the individual will be in the vehicle;
  determining a second weight based on the traffic condition data;
  assigning, via the processor, the first weight to the traffic condition data and the second weight to the test assessment data;
  determining, via the processor, a driver assessment score based on the weighted traffic condition data and the weighted test assessment data, wherein the driver assessment score is associated with a risk of injury associated with an individual driving a vehicle to the destination location in view of the weighted traffic condition data and the weighted test assessment data; and
  sending, via the processor, a request to a ride share system in response to the driver assessment score being below a threshold.

9. The method of claim 8, comprising sending an activation signal to a vehicle control system in response to the driver assessment score being above the threshold, wherein the activation signal is configured to enable the vehicle control system to allow access to control one or more operations of a vehicle.

10. The method of claim 8, wherein receiving the test assessment data comprises receiving an indication of a force against the one or more sensors.

11. The method of claim 8, wherein receiving the test assessment data comprises:
  displaying at least one visual stimulus via an electronic display;
  tracking a movement of an eye in response to the at least one visual stimulus; and
  determining an amount of time associated with the movement of the eye.

12. The method of claim 11, wherein the one or more sensors are configured to track the movement of the eye.

13. The method of claim 8, wherein receiving the trip data comprises mining one or more data sources for the trip data.

14. The method of claim 13, wherein the one or more data sources comprises one or more emails, social media data, or both.

15. The method of claim 8, wherein the computing device comprises a mobile device.

16. The method of claim 8, wherein the traffic condition data comprises an indication of a relative amount of vehicle congestion along a route to the destination location.

17. The method of claim 8, wherein the traffic condition data comprises an indication of an average speed along a route to the destination location.

18. A non-transitory computer-readable medium comprising computer-executable instructions that, when executed by a processor, are configured to cause the processor to perform operations comprising:
  receiving trip data associated with a current location, a destination location, and an expected amount of time that an individual will be in a vehicle for each of one or more routes between the current location and the destination location;
  receiving weather data associated with one or more routes between the current location and the destination location;
  receiving test assessment data indicative of health characteristics of an individual, wherein the test assessment data is determined based on a driving assessment test performed in response to a request from the individual to operate the vehicle;
  determining a first weight based on the expected amount of time that the individual will be in the vehicle;
  determining a second weight based on the weather data;
  assigning the first weight to the weather data and the second weight to the test assessment data to generate weighted weather data and weighted test assessment data;
  determining a driver assessment score based on the weighted weather data and the weighted test assessment data, wherein the driver assessment score is associated with a risk of injury associated with the individual driving a vehicle to the destination location in view of the weighted weather data and the weighted test assessment data;
  determining whether the driver assessment score is above a threshold; and
  sending a signal to a vehicle control system in response to the driver assessment score being above the threshold, wherein the signal is configured to cause the vehicle control system to allow access to control one or more operations of the vehicle.

19. The non-transitory computer-readable medium of claim 18, wherein the computer-executable instructions are configured to cause the processor to perform the operations comprising sending a notification to a computing device in response to the driver assessment score being below the threshold, wherein the notification is indicative of access being denied to the vehicle.

20. The non-transitory computer-readable medium of claim 18, wherein the computer-executable instructions are configured to cause the processor to perform the operations comprising sending a notification to a computing device in response to the driver assessment score being below the threshold, wherein the notification is indicative of a ride being requested by a ride share system.

\* \* \* \* \*